United States Patent
Ludwig et al.

(10) Patent No.: US 6,603,868 B1
(45) Date of Patent: Aug. 5, 2003

(54) METHOD AND APPARATUS FOR PROCESSING AND PLAYBACK OF IMAGES AT A DISPLAY MONITOR

(75) Inventors: Klaus Ludwig, Nuremberg (DE); Gerold Herold, Erlangen (DE); Sebastian Budz, Erlangen (DE)

(73) Assignee: Siemens Aktiengesellschaft, Münich (DE)

(*) Notice: Subject to any disclaimer, the term of this patent is extended or adjusted under 35 U.S.C. 154(b) by 0 days.

(21) Appl. No.: 09/435,442

(22) Filed: Nov. 22, 1999

(30) Foreign Application Priority Data

Nov. 24, 1998 (DE) .......................................... 198 54 241

(51) Int. Cl.[7] .................................................. G06K 9/00
(52) U.S. Cl. ..................................... 382/128; 128/922
(58) Field of Search .............................. 382/128, 154; 128/922; 345/848, 852, 425; 600/407, 425; 359/548, 464; 356/39; 377/10; 378/21; 353/28; 348/57, 53, 510; 709/253; 386/96, 68, 46, 31

(56) References Cited

U.S. PATENT DOCUMENTS

| | | | | |
|---|---|---|---|---|
| 4,879,668 A | * | 11/1989 | Cline et al. ................. | 345/424 |
| 5,170,347 A | * | 12/1992 | Tuy et al. .................... | 345/419 |
| 5,186,176 A | * | 2/1993 | Hiki et al. ................... | 600/440 |
| 5,201,035 A | * | 4/1993 | Stytz et al. .................. | 345/502 |
| 5,371,778 A | * | 12/1994 | Yanof et al. ................... | 378/4 |
| 5,454,371 A | * | 10/1995 | Fenster et al. .............. | 600/443 |
| 5,623,586 A | * | 4/1997 | Hohne ......................... | 345/424 |
| 5,699,446 A | * | 12/1997 | Rougee et al. .............. | 382/130 |
| 5,734,384 A | * | 3/1998 | Yanof et al. ................ | 345/424 |
| 5,891,030 A | * | 4/1999 | Johnson et al. ............. | 128/920 |
| 5,982,953 A | * | 11/1999 | Yanagita et al. ............ | 348/580 |
| 6,104,828 A | * | 8/2000 | Shioiri ........................ | 351/206 |
| 6,211,884 B1 | * | 4/2001 | Knittel et al. ............... | 345/424 |
| 6,266,453 B1 | * | 7/2001 | Hibbard et al. ............. | 382/131 |
| 2002/0031282 A1 | * | 3/2002 | Ideyama ..................... | 382/309 |

FOREIGN PATENT DOCUMENTS

| | | |
|---|---|---|
| DE | PS 42 03 447 | 11/1993 |
| DE | OS 196 15 595 | 10/1997 |

* cited by examiner

*Primary Examiner*—Jayanti K. Patel
*Assistant Examiner*—Barry Choobin
(74) *Attorney, Agent, or Firm*—Schiff Hardin & Waite

(57) ABSTRACT

In a method and apparatus for presentation of images reproducible at a display monitor, digital image data of an examination volume of a subject are registered with an image pickup system, such as a medical examination installation, and at least two images of the examination volume with arbitrary orientation of the image planes relative to one another are simultaneously displayed at the display monitor. At least one marker is contained in each image that indicates information about the position of the image plane of the other image with reference to the image wherein the marking is displayed.

42 Claims, 4 Drawing Sheets

METHOD AND APPARATUS FOR PROCESSING AND PLAYBACK OF IMAGES AT A DISPLAY MONITOR

BACKGROUND OF THE INVENTION

1. Field of the Invention

The present invention is directed to a method and apparatus for the presentation of images reproducible at a display monitor, wherein digital image data of an examination volume of a subject are registered with an image pick-up system such as preferably, a medical examination installation.

2. Description of the Prior Art

Particularly in the field of medical examinations, images of an examination subject that are displayed at a monitor are registered, so that the physician can view them and make a diagnosis based thereon. For example, such images can be registered with a magnetic resonance system, a computed tomography system, an X-ray system or an ultrasound system. When, for example, the head of a patient is to be examined, this is registered in the form of a number of individual tomograms. An examination volume of a subject is registered, i.e. the digital image dataset that is obtained contains not only information about the exterior of the subject but also about of the internal subject volume. As a result, it is possible, for example, to display a head exposure in the form of a volume image, for example as a projection image or as surface image, in three-dimensional form. It is then important for the physician to obtain as much information as possible in an optimally simple way on the basis of the registered images.

SUMMARY OF THE INVENTION

An object of the present invention is to provide a method and apparatus wherein images are displayed at a display monitor that enable the viewer to make an analysis in a simple and surveyable way.

This object is inventively provided in a method (and an apparatus, described below) wherein at least two images of the examination volume with arbitrary orientation of the image planes relative to one another are simultaneously displayed at the display monitor, and wherein at least one marker is displayed in each image that indicates information about the position of the image plane of the other image relative to the image in which the marker is displayed.

According to the inventive method, a number of images of the examination volume, i.e. of the registered subject, are played back at the display monitor, respectively in different image planes, for example, the planes can reside perpendicularly relative to one another, so that the physician obtains an image display in the form of a horizontal section through the examination volume and the other image shows a vertical section. In addition, the physician is provided with information about the image plane setting of the individual images relative to one another in the form of the markings that are mixed into the respective images, so that it is easy for the physician to recognize how the images being displayed are arranged with respect to one another. The physician thus can link the informational contents of the displayed images with one another since each image supplies the physician with a reference to the other image. Inventively, three images can be played back at the monitor, with each image containing two markers relating to the image plane position of the two other images to the image containing the markers. An even greater presentation of information thereby can be achieved.

Inventively, various markers can be employed dependent on the position of the image planes, with a first marker being employed when the image planes reside perpendicularly to one another, and a second marker being employed when the images reside at an angle other than 90° relative to one another. Lines can be displayed as the markers, these markers proceeding substantially over the entire image. When two different markers are employed, the first can be displayed as a solid line and the second can be displayed as a broken line, preferably dashed, or conversely, as long as it is assured that the physician can easily distinguish between the markers.

When more than two images are displayed, it has proven advantageous when an image-specific identifier or a symbol is allocated to each image, with each marker belonging to this image and reproduced in another image likewise showing this identifier or a symbol is allocated thereto, so that a simple reference between a marker displayed in a first image, for example a line, and the appertaining image whose plane orientation is to be indicated, is possible. It has proven essentially expedient to allocate a specific color to each image such as an identifier, particularly in the form of a color frame surrounding the image, with the appertaining marker likewise being reproduced with this color. When, for example, three separate images are used, the first image can exhibit a red frame, the second image a green frame and the third image a blue frame, with a green line and a blue line for indicating the positions of the planes of the second and third images are mixed into the first image, a red line and a blue line for indicating the planes of the first and third images are mixed into the second image, and a red line and a green line referring to first and second images are mixed into the third image.

It has also proven advantageous to provide an auxiliary marking for each line, indicating the direction of view from which the image allocated to the marker is viewed with reference to the image into which that marker is mixed. The auxiliary marker can be in the form of an arrow allocated to the respective line.

Inventively, additional information about the location-related position of the image plane of an image with respect to another image can be provided by means of the marker, for example, where the sectional view through the presentation shown in the first image is the shown, for example, in the second image, position-indicating lines can also be included in the second image. To this end, the respective lines in each image can be presented laterally-shifted or vertically-shifted in an especially simple way, so that the position of the individual images relative to one another can be indicated in a simple way.

So that the physician can evaluate the examination volume in an arbitrary presentation, the orientation of the image plane of an image, and thus the view of the image, can be inventively modified given a correspondingly adapted presentation of the markers. For example, the physician can tilt or rotate a projection image shown as the third image in order to be able to observe the examination volume at a different viewing angle, with the corresponding markers also being automatically adapted or re-adjusted. The modification can expediently ensue by moving the markers, particularly shifting or rotating the lines with a suitable control unit, such as a control mouse. For example, example, a line movement can be accompanied by a modification of the image or presentation. Alternatively or additionally, the modifications of the image plane orientation can ensue with a track ball or the like, i.e. the image presentations themselves are modified and the presentation of the marker is correspondingly adapted. As described, volume images in the form of projection images or surface images or tomograms can be reproduced. The type of image to be reproduced can be selectable, i.e. the user can select whether, for example, projection images or tomograms are to be displayed. The markers always supply the user/viewer with the corresponding information independently of the type of image selected. Different types of image can be simultaneously displayed.

As noted above, the invention is also directed to an apparatus for processing and playback of digital images. The inventive apparatus has an image processor in which the digital image data of an examination volume of a subject are present, and a display monitor for the playback of an image. The apparatus inventively displays at least two images of an examination volume with arbitrary orientation of the image planes relative to one another at the display monitor, and in that the image processor is "fashioned" for generating markers reproducible in the images, with each image containing at least one marker that indicates information about the position of the image plane of the other image with respect to the image in which the marker is displayed. The inventive image processor, which can be a computer means that is capable of processing the digital image data transmitted to it, is designed for generating the respective markers, as well as for reproducing a number of different images at the display monitor. Three images can be reproducible at the display monitor, with the image processor being fashioned for generating and displaying two markers in each image that identify the respective image plane position of the two other images. Further, the image processor can be designed for generating various markers whose type is dependent on the attitude of the image planes. A first marker is employed when, for example, the image planes reside perpendicularly relative to one another; a second marker different in nature from the first marker is employed when the planes reside at an angle other than 90°. Lines that proceed across substantially the entire image can be expediently displayed as the markers. These can be solid or, when different markers are employed, can be broken, for example dashed.

For facilitating the allocation of a marker to a respective image whose plane attitude is to be indicated by the marker (problems occur when four or more images are displayed), the image processor can inventively allocate an image-specific identifier or a symbol for each image, and can likewise allocate this identifier or the symbol to every marker belonging to this image and reproducible in another image. The image processor generates corresponding identifiers or symbols, whereby a specific color, especially in the form of a color frame surrounding the image, is particularly expedient as the image-specific identifier; the appertaining marking is then reproducible in precisely this color. For indicating location-related information in view of the position of the image plane with reference to the presentation of another image, the image processor can also be fashioned for generating markers that additionally contain an information about the location-related position of the image plane of the respective image with respect to a different image, for example in the form of lines displayable side-shifted or height-shifted. Further, it has proven especially expedient for example, the image processor to generate at least one auxiliary marker for each marker, particularly each line, that indicates the direction of view from which the image allocated to the marker is reproduced with reference to the image in which the marker is displayed, particularly in the form of arrows allocated to the line, so that the physician can unproblematically recognize the direction from which the reference image identified by the marking is being viewed relative to the image in which the marking is displayed.

Inventively, further, the orientation of the image plane of an image, and thus the view of the image, is variable given correspondingly adapted presentation of the markers. This can ensue according to a first embodiment of the invention by shifting or moving the markers, i.e. the image presentation here follows the line displacement. Additionally or alternatively, a track ball can be provided with which the image orientation of an image is variable, with the markers being correspondingly modified.

The invention is also directed to a medical examination installation having an image pickup system for registering image data of an examination subject, as well as a device of the aforementioned type to which the image data can be provided in digital form.

DESCRIPTION OF THE PREFERRED EMBODIMENTS

Figure 1:
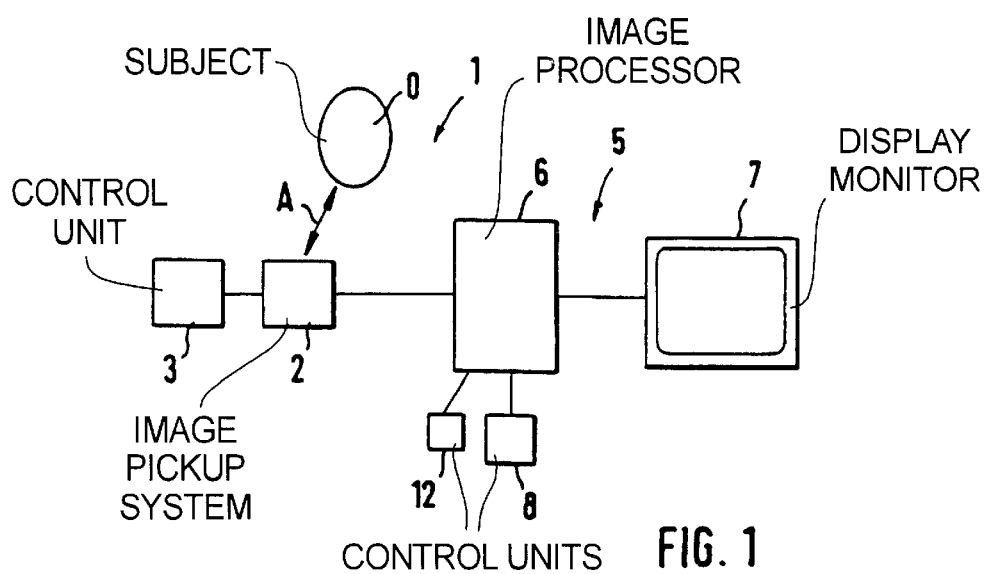
FIG. 1 is a schematic diagram of an inventive medical examination installation having an inventive apparatus.

In a schematic diagram, FIG. 1 shows a medical examination installation 1 having an image pickup system 2 that is controlled by a control unit 3. This is a schematic illustration that shows only the relevant components; it is evident that a medical examination installation also contains a number of other components that are of no significance here. The image pickup system 2 can, for example, be an X-ray system or an ultrasound system; or a magnetic resonance system or a computed tomography system.

The digital image data of a subject O that can be determined with the image pickup system 2, the subject O—as indicated by the double arrow A—being examined. The digital data are forwarded to an apparatus for processing and playback of registered images 5, containing an image processor 6 as well as a display monitor 7. The images can be output at the display monitor. Further, a control unit 8 in the form of a control mouse, with which markers displayable at the display monitor 7 are movable, is allocated to the image processor 6, as discussed below. Moreover, a further control unit 12, for example in the form of a track ball with which the image orientation is variable, is provided.

Figure 2:
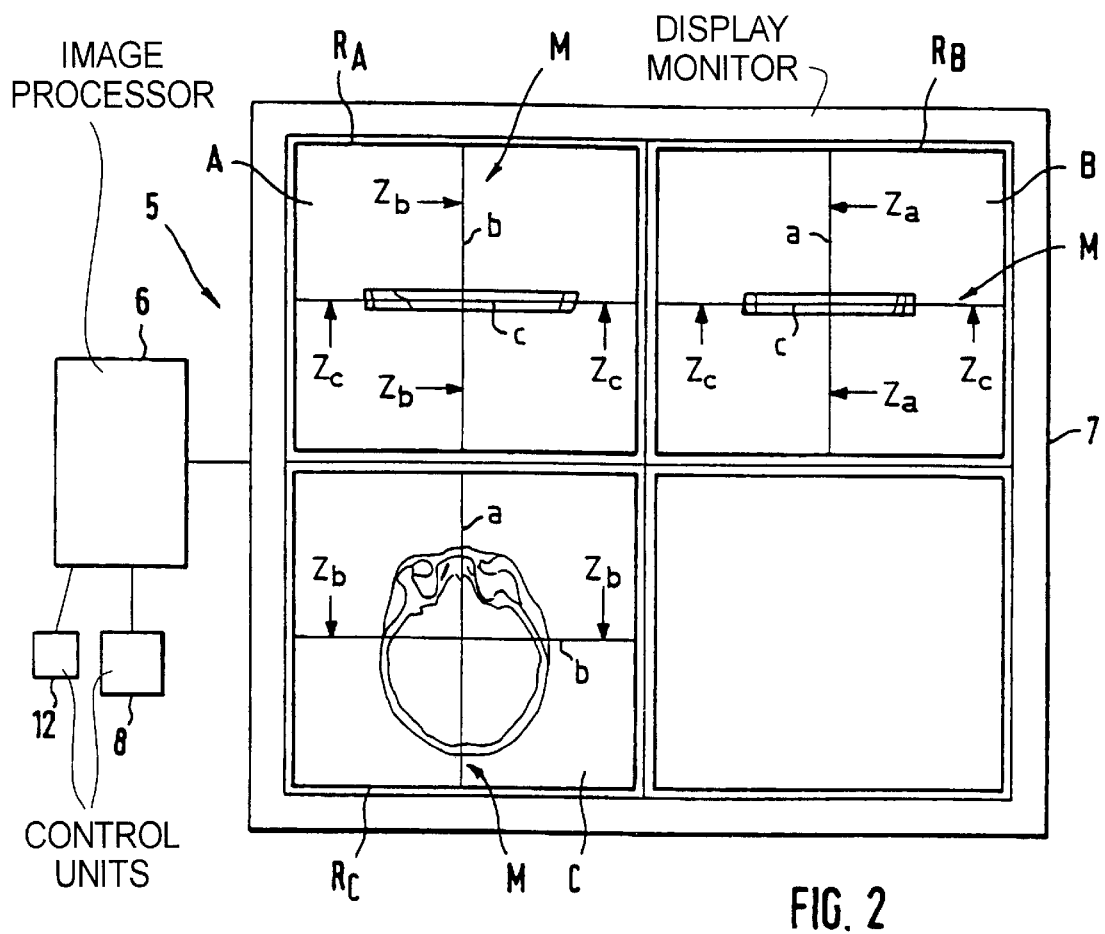
FIG. 2 is a schematic diagram of the inventive apparatus showing images presented at the display monitor FIGS. 3–7 respectively show illustrations of the processed images reproducible at the display monitor.

FIG. 2 in the form of a schematic diagram, shows the inventive apparatus having the image processor 6 as well as the two allocated control units 8, 12 and the display monitor 7. Three images A, B, C of an examination volume are shown thereat as an example. A slice of a head exposure was shown here as examination volume. As a rule, the entire head is registered in terms of image orientation. This ensues such that individual head slices are respectively registered, the overall head presentation being composed of these slices. The image C shows a view of the slice looking from below, i.e. proceeding from the feet onto the slice; image A shows a longitudinal section through the slice shown in image C, and image B shows a cross-section. Each of the images A, B, C is provided with an image-specific identifier in the form of a colored image frame, i.e. a specific color identification is allocated to each image. In FIG. 2, these color frames are identified as $R_A$, $R_B$, $R_C$. For example, the frame $R_A$ is red, the frame $R_B$ is green and the frame $R_C$ is blue.

As also can also be seen from FIG. 2, a plurality of markings M in the form of the illustrated lines are reproduced in each image A, B, C. These lines indicate the attitude of the image planes of the respective reference image allocated to the line with respect to the image in which the lines are reproduced. The line b entered in image A, which proceeds vertically here, indicates the attitude of the image plane of the image B with respect to the image A; the line c indicates the attitude of the image plane of the image C. The situation is similar in images B and C; in image B, the line a indicates the position of the image A, the line c indicates that of the image C and the line a in the image C identifies the plane attitude of the image A and the line b identifies the plane attitude of the image B. The lines A, B, C are displayed colored according to the color of the respective image frame $R_A$, $R_B$ or $R_C$ in order to enable a distinction between them and for allocating the respective reference image A, B or C.

In the exemplary embodiment, the image planes of all three of the images reside perpendicularly relative to one another in the three-dimensional space. The perpendicular plane position is indicated in that the lines a, b, c are solid. On the basis of the lines a, b, c, the physician can thus recognize how the images A, B, C reside relative to one another. In order to also recognize from what direction each image is being viewed, for example, the image C with respect to the image A, the auxiliary markers Z in the form of arrows are allocated to the respective lines a, b, c, these being the same color as the respective line. The auxiliary markers are identified as $Z_A$, $Z_B$ and $Z_C$ in the illustrated example. Image C, accordingly, represents, for example, a view of the slice-shaped examination volume looking onto the slice shown in image A from below.

FIGS. 3 through 7, which only show the image presentations at the display monitor 7 for simplicity, show various modifications of the image presentations proceeding from the initial situation shown in FIG. 2.

Figure 3:
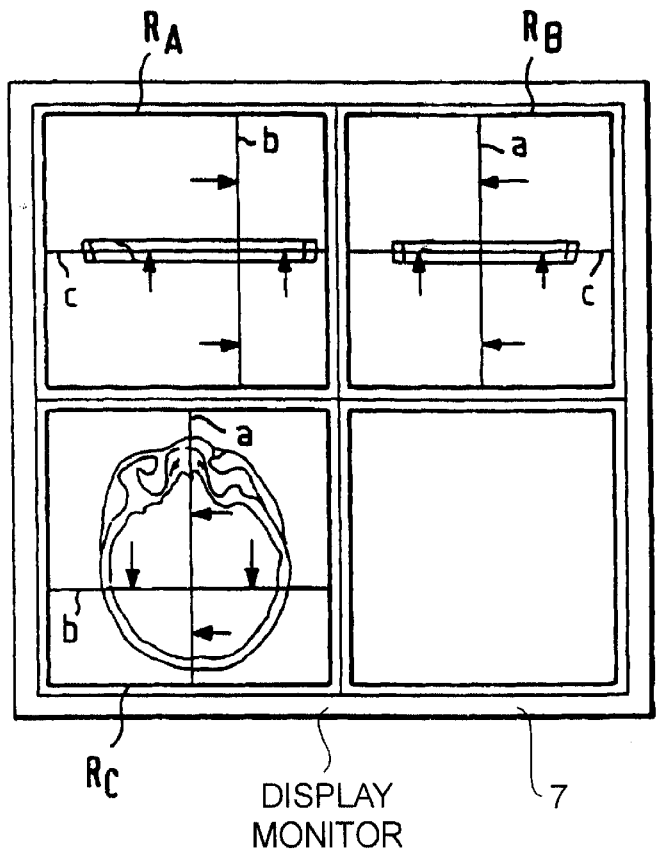

The position of the image plane of the image B has been modified in FIG. 3, this being indicated by the modified position of the respective lines b in the images A and C. In the illustrated example, the image plane of the image B was shifted "down" with respect to the image C; in specific terms, meaning that the image plane shows a presentation from the examination volume in the region of the back of the head. Correspondingly, the line b is shifted toward the right in image A. As already stated, image A shows a longitudinal section through the subject shown in image C. Since image B was shifted and since image B resides perpendicularly on image A, thus a shift to the line b toward the right must also necessarily occur in image A. Even though the image plane of the image B was shifted here, all images continue to reside perpendicularly on one another, as indicated by the solid lines a, b and c.

Figure 4:
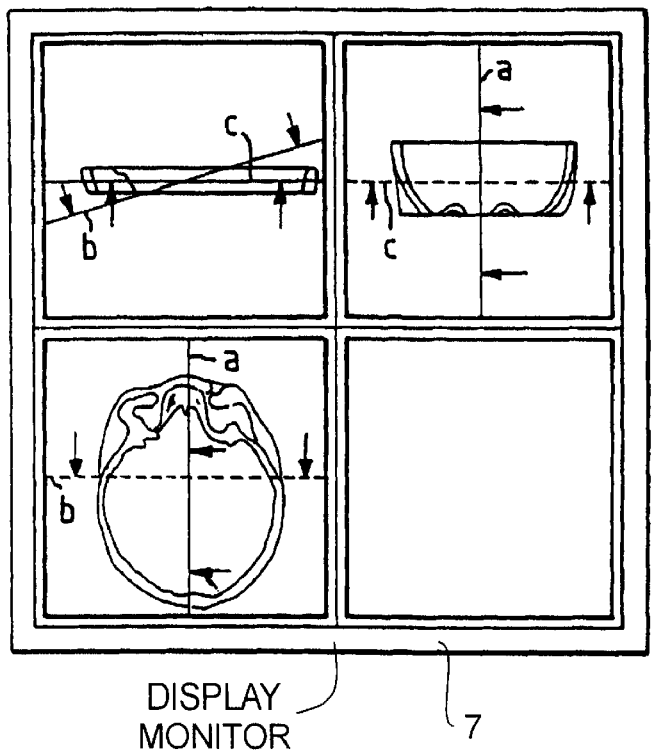

FIG. 4 then shows the situation—proceeding from FIG. 2—wherein the presentation in the image B is tilted, such that the image planes of images A and B continue to reside perpendicularly on one another but image B and C no longer reside perpendicularly relative to one another. With respect to the presentation of the markings, this results in the line c in the image B being broken, since the planes no longer reside perpendicularly on one another here; likewise, the line b in the image C is shown broken. The images A and C likewise continue to reside perpendicularly on one another, for which reason the lines a, c with respect thereto are shown solid. The modification of the presentation of the image B can ensue simply by rotating the line b in the image A with the control unit 8; the orientation of the image B is then also set in conformity with the line motion.

Figure 5:
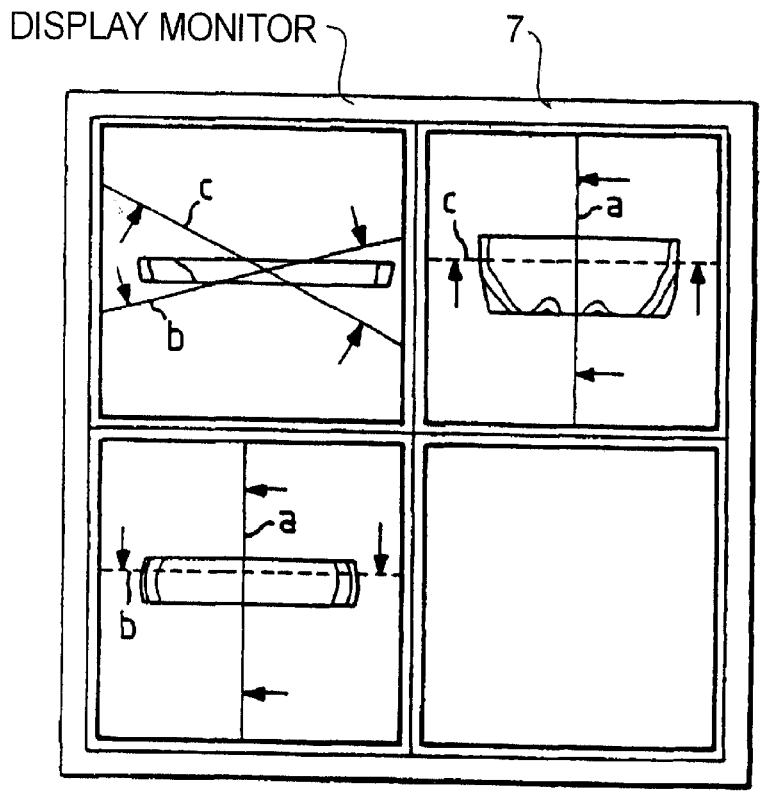

Proceeding from the graphic illustration in FIG. 4, the orientation of the image plane of the image C is now modified in FIG. 5 by rotating the line c in image A. Corresponding with the positioning of the line c, the presentation in image C is now also modified, i.e. since the line c no longer proceeds horizontally through the subject shown in image A but intersects this at an angle, only that region of the subject is likewise visible in image C that is visible given observation of the subject shown in image A from the angle prescribed by the line attitude. In the image C, this is now only the narrow portion through the head, with only the skull sides, but no longer the front and back of the head, being visible. The image planes of the images A and C continue to reside perpendicularly on one another, for which reason the lines are solid. This operation has changed nothing regarding the orientation of the image B relative to the images A and C.

Figure 6:
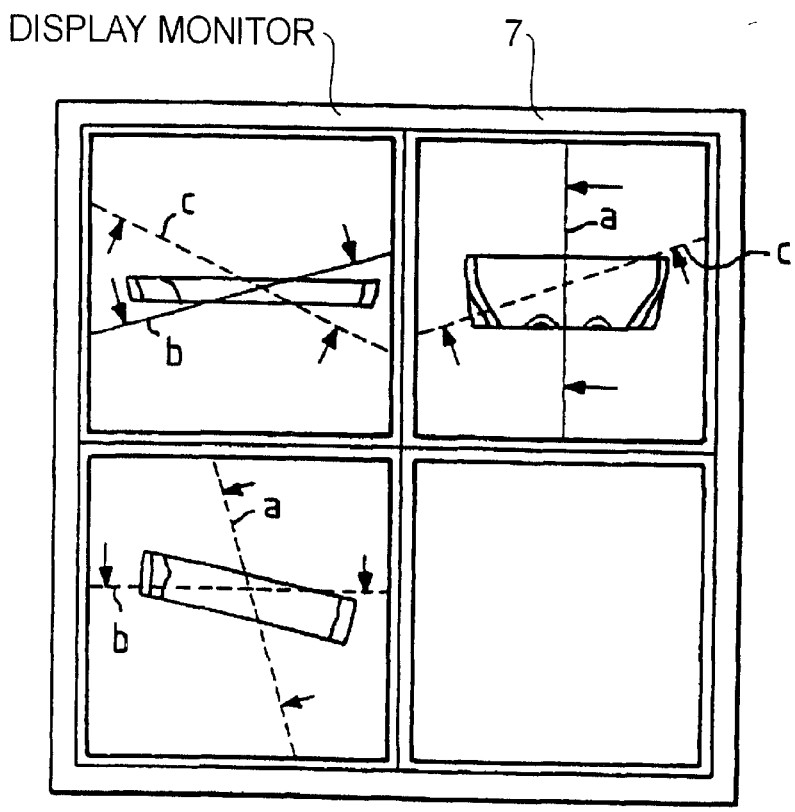

FIG. 6 shows a further illustration proceeding from FIG. 5, wherein the line c is rotated in the image B. This leads to the fact that the image C is varied in terms of its orientation such that the image plane of the image C now no longer resides perpendicularly on the image A. This is expressed on the display monitor 7 by the lines c in the image A and a in the image C likewise being shown broken. As a consequence of the variation of the line c in the image B and the change in orientation of the image plane of the image C which accompanies this, an attitudinal change of the line a in image c now also occurs, such that this is tilted somewhat toward the left. Image A, however, continues to reside perpendicularly on image B here.

Figure 7:
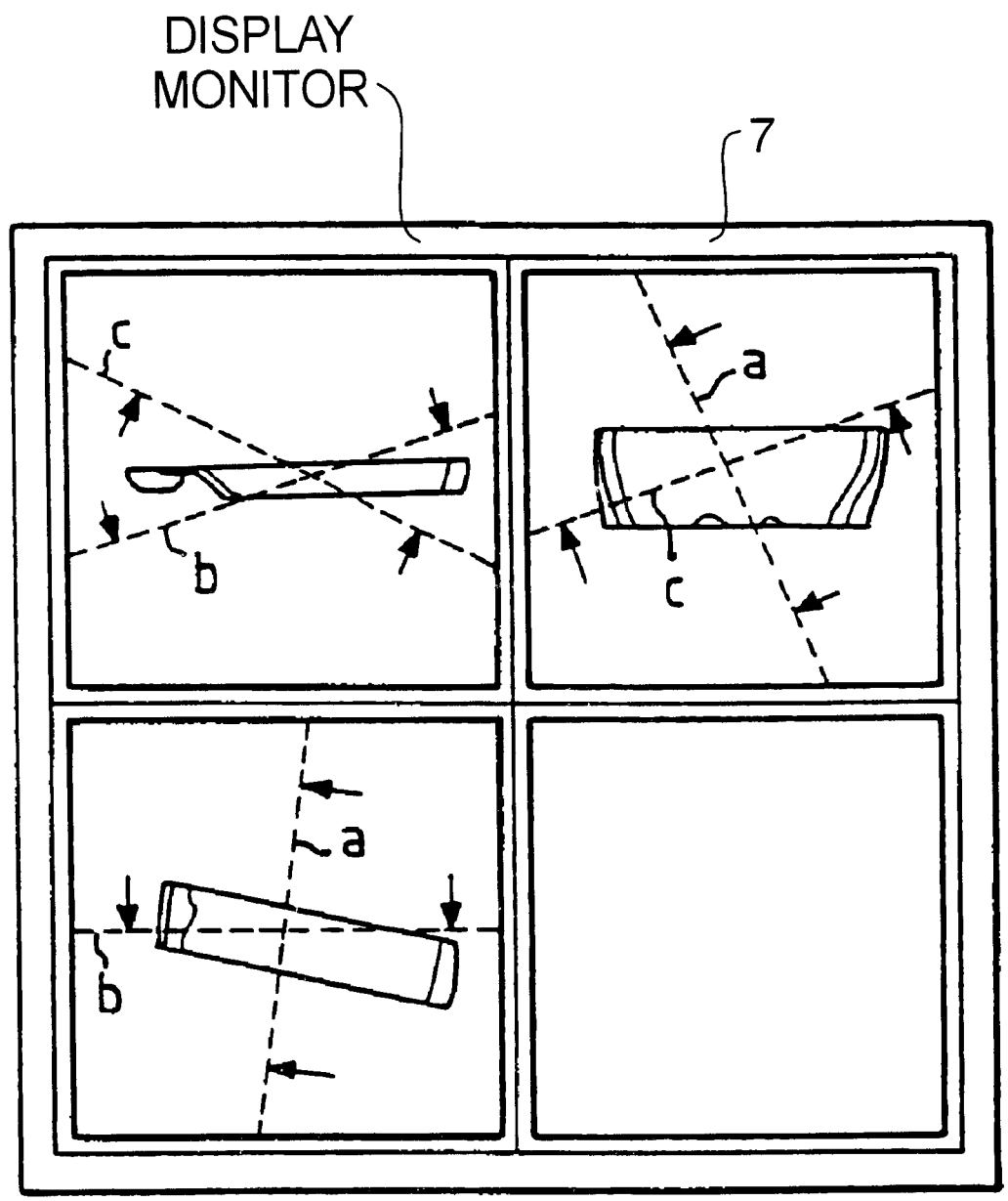

FIG. 7 shows an image presentation wherein none of the image planes reside perpendicularly on one another. This produces the greatest degree of complexity; all images A, B, C are arbitrarily oriented in the three-dimensional space. Given the presentations shown in FIG. 7, the line a has been rotated in image B, causing the corresponding presentation in image A also to be modified. Due to the rotation, the planes of the images A, B no longer reside perpendicularly relative to one another, for which reason the lines b in image A and a in image B are shown broken as well. As a consequence of the modification of the presentation of the image A accompanying the movement of the line a in image B, the course of the line a in the image C also changes. The lines make it possible for each image can be employed as a reference for the two other images whose lines are displayed on the reference image.

As described, the generation of the respective images as well as of the markers ensues in the image processor, which is fashioned in conformity therewith. The modification of the respective image presentations, which the physician undertakes in order to obtain corresponding sectional views, can—as described—ensue, for example, by moving the lines with the control unit 8, i.e., for example, the control mouse. Alternatively, the variation of the image presentation can ensue with the other control unit 12, for example in the form of a track ball. Here, the image is modified; the presentation of the lines then ensues on the basis of the modified image; i.e., the operating mode is exactly opposite here.

In the illustrated examples, the images A, B and C are shown as projection images which effectively allow a view through the illustrated examination volume. The physician, however, can select whatever type of image he or she would like to have displayed, for example with one of the control units 8, 12. For example, the physician can have the examination volume displayed with surface images instead of projection images. A mixed presentation, for example images A and B as projection images, image C as a surface image, is also possible. Regardless of the type of image selected, the markers are mixed into every image, i.e. it is possible for the physician to orient himself or herself on the basis of the marker in any arbitrary image presentation.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for presenting images at a display monitor comprising the steps of:
    obtaining digital image data of an examination volume of a subject with an image pick-up system;
    simultaneously displaying at least two images, reproduced from said digital image data, of said examination volume at a display monitor, each of said images being presented in an image plane with the respective image planes of said at least two images being arbitrarily oriented relative to each other; and
    in each of said at least two images, including a marker which indicates a position of the image plane in another of said at least two images with respect to the image plane of the image containing the marker.

2. A method as claimed in claim 1 comprising displaying three images simultaneously at said display monitor, each of said three images having an image plane with the respective image planes of said three images being arbitrarily oriented relative to each other, and wherein each of said three images contains two markers, respectively indicating the position of the respective image planes of the other two of said three images relative to the image plane of the image containing the marker.

3. A method as claimed in claim 1 comprising displaying said marker with a first form to indicate respective images planes oriented perpendicularly to each other, and displaying said marker with a second form to indicate respective image planes oriented at a non-90° degree angle relative to each other.

4. A method as claimed in claim 3 wherein said marker comprises lines.

5. A method as claimed in claim 4 wherein said lines proceed substantially across an entirety of the image containing the lines.

6. A method as claimed in claim 4 comprising displaying said lines as solid lines as said first form and displaying said lines as broken lines as said second form.

7. A method as claimed in claim 4 comprising displaying said lines as broken lines as said first form and displaying said lines as solid lines as said second form.

8. A method as claimed in claim 1 wherein said marker comprises lines.

9. A method as claimed in claim 8 wherein said lines proceed substantially across an entirety of the image containing the lines.

10. A method as claimed in claim 1 comprising the additional step of displaying, as a part of the respective marker in each of said at least two images, an image-specific identifier identifying with which said at least two images said marker is associated.

11. A method as claimed in claim 10 comprising displaying each marker with an image-specific color as said image-specific identifier.

12. A method as claimed in claim 11 comprising displaying said at least two images respectively surrounded by respective color frames, said respective color frames having a color corresponding to said image-specific color of the marker in the image surrounded by that color frame.

13. A method as claimed in claim 1 comprising displaying information, as a part of the respective markers in said at least two images, identifying a positional location of the image plane contained in the respective image.

14. A method as claimed in claim 13 wherein said marker comprises lines, and wherein said lines are displayed laterally-shifted or vertically-shifted in the respective image to provide said positional location information.

15. A method as claimed in claim 1 comprising the additional step of displaying, in each of said two images, an auxiliary marker indicating a direction of view from which the image associated with the marker is displayed.

16. A method as claimed in claim 15 wherein said marker comprises lines and wherein said auxiliary marker comprises arrows respectively associated with the lines.

17. A method as claimed in claim 1 comprising changing an orientation of the image plane in at least one of said at least two images, to produce a changed-orientation image on said display monitor, and automatically adapting the marker in said another of said at least two images on said display monitor to indicate the change in orientation of said changed-orientation image.

18. A method as claimed in claim 17 wherein said marker comprises lines, and wherein the step of adapting said marker for said changed-orientation image comprises re-orienting said lines, in a manner selected from the group consisting of linearly displacing said lines and rotating said lines, using a control element.

19. A method as claimed in claim 17 comprising changing said image plane of at least one of said at least two images with a track ball connected to said display.

20. A method as claimed in claim 1 comprising displaying said at least two images as images selected from the group consisting of projection images, surface images, and tomograms.

21. A method as claimed in claim 20 comprising optionally selecting, for each of said at least two images, which of said images in said group will be displayed.

22. An apparatus for presenting images comprising the steps of:
    an image pick-up system which obtains digital image data of an examination volume of a subject;
    a display, monitor; and
    an image processor for simultaneously displaying at least two images reproduced from said digital image data, of said examination volume at said display monitor, each of said images being presented in an image plane with the respective image planes of said at least two images being arbitrarily oriented relative to each other, and for, in each of said at least two images, including a marker which indicates a position of the image plane in another of said at least two images with respect to the image plane of the image containing the marker.

23. An apparatus as claimed in claim 22 wherein said image processor displays three images simultaneously at said display monitor, each of said three images having an image plane with the respective image planes of said three images being arbitrarily oriented relative to each other, and wherein said image processor generates two markers in each of said three images, said two markers respectively indicating the position of the respective image planes of the other two of said three images relative to the image plane of the image containing the marker.

24. An apparatus as claimed in claim 22 wherein said image processor displays said marker with a first form to indicate respective images planes oriented perpendicularly to each other, and displays said marker with a second form to indicate respective image planes oriented at a non-90° degree angle relative to each other.

25. An apparatus as claimed in claim 24 wherein said image processor displays said marker as lines.

26. An apparatus as claimed in claim 25 wherein said image processor displays as lines proceeding substantially across an entirety of the image containing the lines.

27. An apparatus as claimed in claim 25 wherein said image processor displays said lines as solid lines as said first form and displaying said lines as broken lines as said second form.

28. An apparatus as claimed in claim 25 wherein said image processor displays said lines as broken lines as said first form and displaying said lines as solid lines as said second form.

29. An apparatus as claimed in claim 22 wherein said image processor displays said marker comprises lines.

30. An apparatus as claimed in claim 29 wherein said image processor displays as lines proceeding substantially across an entirety of the image containing the lines.

31. An apparatus as claimed in claim 22 wherein said image processor additionally displays, as a part of the respective marker in each of said at least two images, an image-specific identifier identifying with which said at least two images said marker is associated.

32. An apparatus as claimed in claim 31 wherein said image processor displays each marker with an image-specific color as said image-specific identifier.

33. An apparatus as claimed in claim 32 wherein said image processor displays said at least two images respectively surrounded by respective color frames, said respective color frames having a color corresponding to said image-specific color of the marker in the image surrounded by that color frame.

34. An apparatus as claimed in claim 22 said image processor additionally displays, as a part of the respective markers in said at least two images, identifying a positional location of the image plane contained in the respective image.

35. An apparatus as claimed in claim 34 wherein said image processor displays said marker as lines, and wherein said lines are displayed laterally-shifted or vertically-shifted in the respective image to provide a said positional location information.

36. An apparatus as claimed in claim 22 said image processor additionally displays, in each of said two images, an auxiliary marker indicating a direction of view from which the image associated with the marker is displayed.

37. An apparatus as claimed in claim 36 wherein said image processor displays said marker as lines and wherein said image processor displays said auxiliary marker as arrows respectively associated with the lines.

38. An apparatus as claimed in claim 22 comprising an input unit connected to said image processor for changing an orientation of the image plane in at least one of said at least two images, to produce a changed-orientation image on said display monitor, and wherein said image processor automatically adapts the marker in said another of said at least two images to indicate the change in orientation of said changed-orientation image.

39. An apparatus as claimed in claim 38 wherein said image processor displays said marker as lines, and wherein said image processor adapts said marker for said changed-orientation image by re-orienting said lines, in a manner selected from the group consisting of linearly displacing said lines and rotating said lines, using a control element connected to said image processor.

40. An apparatus as claimed in claim 38 comprising a track ball connected to said image processor for changing said image plane of at least one of said at least two images.

41. An apparatus as claimed in claim 22 wherein said image processor displays said at least two images as images selected from the group consisting of projection images, surface images, and tomograms.

42. An apparatus as claimed in claim 41 comprising an input unit connected to said image processor for selecting, for each of said at least two images, which of said images in said group will be displayed.

* * * * *